US005540825A

United States Patent [19]
Yeung et al.

[11] Patent Number: 5,540,825
[45] Date of Patent: Jul. 30, 1996

[54] NOISE SUPPRESSING CAPILLARY SEPARATION SYSTEM

[75] Inventors: Edward S. Yeung, Ames, Iowa; Yongjun Xue, Norwich, N.Y.

[73] Assignee: Iowa State University Research Foundation, Inc., Ames, Iowa

[21] Appl. No.: 406,714

[22] Filed: Mar. 20, 1995

Related U.S. Application Data

[63] Continuation-in-part of Ser. No. 101,143, Aug. 2, 1993, abandoned.

[51] Int. Cl.$^6$ .................. G01N 27/26; G01N 27/447; G01N 21/85; G01N 30/62
[52] U.S. Cl. .................. 204/452; 204/603; 356/344; 356/435; 73/61.58; 73/23.4
[58] Field of Search .................. 204/299 R, 180.1; 356/344, 435; 73/61.58, 23.4

[56] References Cited

U.S. PATENT DOCUMENTS

| 2,220,231 | 4/1972 | Riebling | 257/356 |
|---|---|---|---|
| 5,047,134 | 9/1991 | Weinberger et al. | 204/299 |
| 5,134,276 | 7/1992 | Hobbs | 250/208 |
| 5,202,006 | 4/1993 | Chen | 204/180 |

FOREIGN PATENT DOCUMENTS

| 2220231 | 10/1973 | Germany | 356/435 |
|---|---|---|---|

OTHER PUBLICATIONS

A. G. Ewing et al., "Capillary Electrophoresis," *Anal. Chem.*, 61, 292A–303A (1989).

K. L. Haller et al., "Double Beam Laser Absorption Spectroscopy: Shot Noise–Limited Performance at Baseband with a Novel Electronic Noise Canceller," *SPIE Proc.*, 1435, 298–309 (1991).

T. Higashijima et al., "Determination of Amino Acids by Capillary Zone Electrophoresis Based on Semiconductor Laser Fluorescence Detection," *Anal. Chem.*, 64, 711–714 (1992).

P. C. D. Hobbs, "Reaching the Shot Noise Limit for $10," *Optics and Photonics News*, 17–23 (Apr. 1991).

P. C. D. Hobbs, "Shot Noise Limited Optical Measurements at Baseband with Noisy Lasers," *SPIE Proc.*, 1376, 216–221 (1991).

S. Mho et al., "Detection Method for Ion Chromatography Based on Double–Beam Laser–Excited Indirect Fluorometry," *Anal. Chem.*, 57(12), 2253–2256 (1985).

J. A. Taylor et al., "Axial–Beam Absorbance Detection for Capillary Electrophoresis," *J. Chromatogr.*, 550, 831–837 (1991).

S. J. Williams et al., "Diode Laser–Based Indirect Absorbance Detector for Capillary Electrophoresis," *J. of Chromatography*, 636, 39–45 (1993).

E. S. Yeung et al., "Indirect Detection Methods for Capillary Separations," *Anal. Chem.*, 63, 275A–282A (1991).

David M. Goodall et al, "Diode laser–based indirected absorbance detector for capillary electrophoresis" Journal of Chromatography 636 (Apr. 23, 1993) 39–45.

Totaro Imasaka et al, "Determination of Amino Acids by Capillary Zone Electrophoresis Based on Semiconductor Laser Fluorescence Detection" Analytical Chemistry, vol. 64, No. 7 (Apr. 1, 1992) 711–714.

*Primary Examiner*—John Niebling
*Assistant Examiner*—John S. Starsiak, Jr.
*Attorney, Agent, or Firm*—Schwegman, Lundberg & Woessner, P.A.

[57] ABSTRACT

A noise-suppressing capillary separation system for detecting the real-time presence or concentration of an analyte in a sample is provided. The system contains a capillary separation means through which the analyte is moved, a coherent light source that generates a beam which is split into a reference beam and a sample beam that irradiate the capillary, and a detector for detecting the reference beam and the sample beam light that transmits through the capillary. The laser beam is of a wavelength effective to be absorbed by a chromophore in the capillary. The system includes a noise suppressing system to improve performance and accuracy without signal averaging or multiple scans.

18 Claims, 12 Drawing Sheets

NOISE SUPPRESSING CAPILLARY SEPARATION SYSTEM

GOVERNMENT RIGHTS

This work was made with Government support under Contract No. W-7405-Eng-82 awarded by the Department of Energy. The Government has certain rights in the invention.

RELATED APPLICATIONS

This application is a continuation-in-part of U.S. patent application Ser. No. 08/101,143, filed on Aug. 2, 1993 now abandoned titled SPLIT BEAM NOISE SUPPRESSING CAPILLARY SEPARATION SYSTEM, which is hereby incorporated by reference.

FIELD OF THE INVENTION

The present invention relates to the field of detecting analytes in an analytical sample using a capillary separation system. More particularly, the present invention relates to apparatus and methods for the detection of analytes in samples using a capillary separation system incorporating a noise suppression system.

BACKGROUND OF THE INVENTION

Capillary electrophoresis (CE) is one of the most powerful separation methods. Analysis can be conducted even when samples are sub-nanoliter in volume (Ewing, A. G.; Wallingford, R. A.; Olefirowicz, T. M., *Anal. Chem.*, 61, 292A–303A, 1989).

In capillary electrophoresis, a capillary containing buffer is suspended between two reservoirs filled with buffer. An electric field is applied across the two ends of the capillary. Analytes in a sample introduced at the high potential end migrate toward the low potential end under the influence of the electric field. Typically, capillary electrophoresis is carried out with a 0–60 KV DC power supply. When an analyte is about to exit the capillary, it can be detected by various techniques.

Commonly used methods for detecting analytes in CE include absorption, fluorescence, electrochemical, and mass spectrometric detection (Ewing et al. supra). Among these methods, UV-vis absorption detectors are the most popular because of their versatility and simplicity, and because they are usually supplied with commercial CE systems.

However, on-column absorption schemes in CE can only detect about $10^{-5}$M to $10^{-6}$M of an analyte in a sample due to the limited pathlength, low intensity, and the presence of stray light when using an incoherent light source (Bruin, G. J. M.; Stegeman, G.; Van Asten, A. C.; Xu, X.; Kxaak, J. C.; Poppe, H. J., *Chromatogr.*, 559, 163–181, 1991).

One way to improve the detection limit in CE is to increase the effective pathlength. Taylor and Yeung increased the effective pathlength of their absorbance detectors by directing the light beam along the capillary axis to obtain an approximately 60-fold improvement in the pathlength (Taylor, J. A.; Yeung, E. S., *J. Chromatogr.*, 550, 831–837, 1991). The reduced zone lengths associated with CE unit axial beam detection and the choice of electrolytic buffers is limited to those with a refractive index higher than that of the column walls.

Liquid chromatography (LC) is also a powerful analytical technique. LC separates analytes in a mixture based on the repetitive distribution of the molecules of the analytes between a mobile and a stationary phase. The mobile phase is a liquid through which the analytes pass. In high-performance liquid chromatography (HPLC), the driving force for the movement of liquid and analytes is primarily the pressure difference between the two ends of the chromatographic column. Mho and Yeung disclosed a detection method for ion chromatography based on double-beam Laser-Excited Indirect Fluorometry (Mho, S.; Yeung, E. S.; *Anal. Chem.*, 57(12), 2253–2256, 1985). Detection methods based on absorption for analytes in LC are similar to those used in CE. As with any absorption measurement, noise reduction will lead to increased sensitivity.

Lasers are not widely used in conjunction with CE or LC because of their instability which increases noise, thereby hindering the detection of low analyte concentrations in small samples. One way of reducing noise is to use a dual beam detector system. In a conventional double-beam absorption detector, the light output is split into a sample and a reference beam. The resulting photocurrents, or voltages, are either subtracted from each other or divided. Subtraction requires extremely fine adjustment of the two beams to equal intensities and requires identical detector and amplifier characteristics for good noise suppression. An analog divider is typically used for conventional division and suffers from the poor performance.

Hobbs, et al. describe a double-beam laser absorption system based on all-electronic noise suppression (Hobbs, P. C. D., *SPIE Proc.*, Roy, R., Ed., 1376, 216–221, 1991; Haller, K. L. and Hobbs, P. C. D., *SPIE Proc.*, Feary, B. L., Ed., 1435, 298–309, 1991; Hobbs, P. C. D., *Optics & Photonics News*, 17–23, April 1991). The system functions by subtracting the signal from the reference photocurrents under feedback control to cancel spurious modulation of the laser beam and excess noise, which is the noise above the shot-noise level. Multiple spectral scans of a sample in a cell containing $I_2$ were subjected to analog low frequency (100 Hz high pass) filtering and signal-averaging (1000 individual sweeps) to achieve a noise-equivalent absorption (i.e., noise in absorption) of $2 \times 10^{-7}$ (Haller, K. L. and Hobbs, P. C. D., *SPIE Proc.*, Feary, B. L., Ed., 1435, 298–309, 1991).

Hobbs (U.S. Pat. No. 5,134,276) discloses electrical circuits for noise suppression in such a system. The systems described by Hobbs et al. in the aforementioned documents were, however, applied in spectroscopy and are not related to CE or LC, which are low frequency operations.

To achieve noise reduction, Hobbs et al. scanned the output repetitively and averaged the signals. While that process may improve the output accuracy, it prevents the system from providing "real-time" or "on-column" data of the changing levels of analyte in the sample. Furthermore, in technologies such as biotechnology, analyses often have to be conducted on samples which are small in volume and contain very dilute analytes. By requiring multiple scans, such systems may not be able to accurately analyze small, dilute samples.

As a result, there is a need for a capillary separation system which is capable of providing highly sensitive, real-time detection of analytes which may be dilute and/or provided in small samples.

SUMMARY OF THE INVENTION

The present invention provides a noise-suppressing capillary separation system (NSCSS) for detecting the real-time presence or concentration of an analyte in an analytical sample.

The NSCSS comprises a capillary separation means, such as CE or LC for moving the analyte through a capillary, a source of coherent light for providing a coherent light beam that is split into a reference beam and a sample beam which irradiates and is transmitted through the capillary, and a detector for detecting the reference beam and the transmitted light through the capillary.

The invention also includes a noise suppressing electrical circuit for noise suppression by electronically subtracting current derived from the detected reference beam from current derived from the light transmitted through the capillary. As used herein, the term "subtracting" refers to finding the difference between two values.

Further, the present invention is also directed to a method of improving the real-time detection of the presence or concentration of an analyte in a sample analyzed in a capillary separation means. In this method, a coherent light beam is split into a reference beam and a sample beam to irradiate the sample in the capillary. The reference beam and the transmitted light through the capillary are detected with a detector having a noise suppressing electrical circuit.

The NSCSS according to the present invention provides a number of advantages over known noise suppression systems for capillary separation systems.

The analyte can be detected by the present invention in "real time" and "on column" as the analyte passes through the capillary, i.e. any change of concentration of the analyte as it passes through the detection zone of the capillary can be detected essentially immediately without having to sample from the capillary for later analysis or signal average to reduce noise.

There is no need to carefully match electronic components used in the systems according to the present invention. The only requirements are a matched differential pair, a large collector coefficient B, and operation in the active region. As long as each of the photodiodes is in the linear response range, the photodiodes need not even be matched.

There is also no need for careful tuning of the electronics because the negative feedback can be applied to keep the net DC photocurrent at zero to result in noise cancellation and shot-noise limited performance.

The NSCSS of the present invention is particularly well-suited for noise suppression in a low frequency analytical method such as CE or LC. Typically, the elution of analytes in the capillary is slow enough that data points do not have to be collected more frequently than once every second. Using the NSCSS of the present invention, significant noise suppression can be achieved without multiple scans and signal-averaging, thereby increasing the response of the system for better real-time data.

Noise can typically be suppressed to 10 times the shot-noise-limited level without signal-averaging when using the NSCSS and methods of the present invention. If desired, however, signal-averaging can be performed electronically or manually by averaging data from multiple measurements in the application of the present invention, such signal-averaging is not necessary to realize the noise suppression benefits of the invention.

The present invention can be used to measure analytes such as inorganic ions and organic ions. The presence or concentration of biochemical substances, such as polypeptides, polynucleotides, carbohydrates, cells, bacteria, and viruses can be determined by utilizing the present invention. Derivatives can be made from these substances for separation using CE or LC. Using the direct absorption CE method of the present invention, an analyte can be detected at a concentration that is about 10 to about 100 times the analyte concentration that is 8 shot-noise-limited, typically in the range of about $10^{-8}$M to about $10^{-7}$M.

Direct absorption of laser light is generally thought to be inappropriate in CE because lasers are typically highly unstable (±0.1% in ideal cases), degrading the dynamic reserve of the system, thus causing difficulties in detection. However, CE, particularly indirect absorption CE, is useful for detecting analytes in small samples. For example, in the analysis of single cells, there is often a limited supply of sample.

The increased sensitivity of NSCSS according to the present invention can be advantageously utilized to detect small samples in a capillary with a small i.d. Using the present invention in indirect absorption in CE, an analyte can be detected at a concentration that is about 20 to about 200 times the analyte concentration that is shot-noise-limited, typically in the range of about $10^{-7}$M to about $10^{-6}$M. Likewise, the present invention increases the sensitivity of detecting an analyte using LC when compared to conventional LC detection systems.

The detection limit is inversely proportional to the capillary inside diameter. Even with capillaries as small as about 20 μm in inside diameter, using a laser beam diameter of about 10 μm, there is little alignment noise. Comparatively, the sensitivity in commercially available detectors deteriorates much faster with the decrease of capillary diameter. With commercial systems, a capillary smaller than 50 μm i.d. does not usually provide good sensitivity.

In systems according to the present invention, the collimated laser beam can easily be focused down to a spot of a few micrometers. In this way, almost all of the light passes through the inside core of the capillary along a diameter and Beer's Law will hold, resulting in low noise compared to commercial systems. This is true for capillaries in the NSCSS of as small as 20 μm i.d. or less.

For a better understanding of the features and advantages according to the present invention, reference should be made to the following description of the preferred embodiments and methods.

DETAILED DESCRIPTION OF THE PREFERRED EMBODIMENTS

Figure 1:
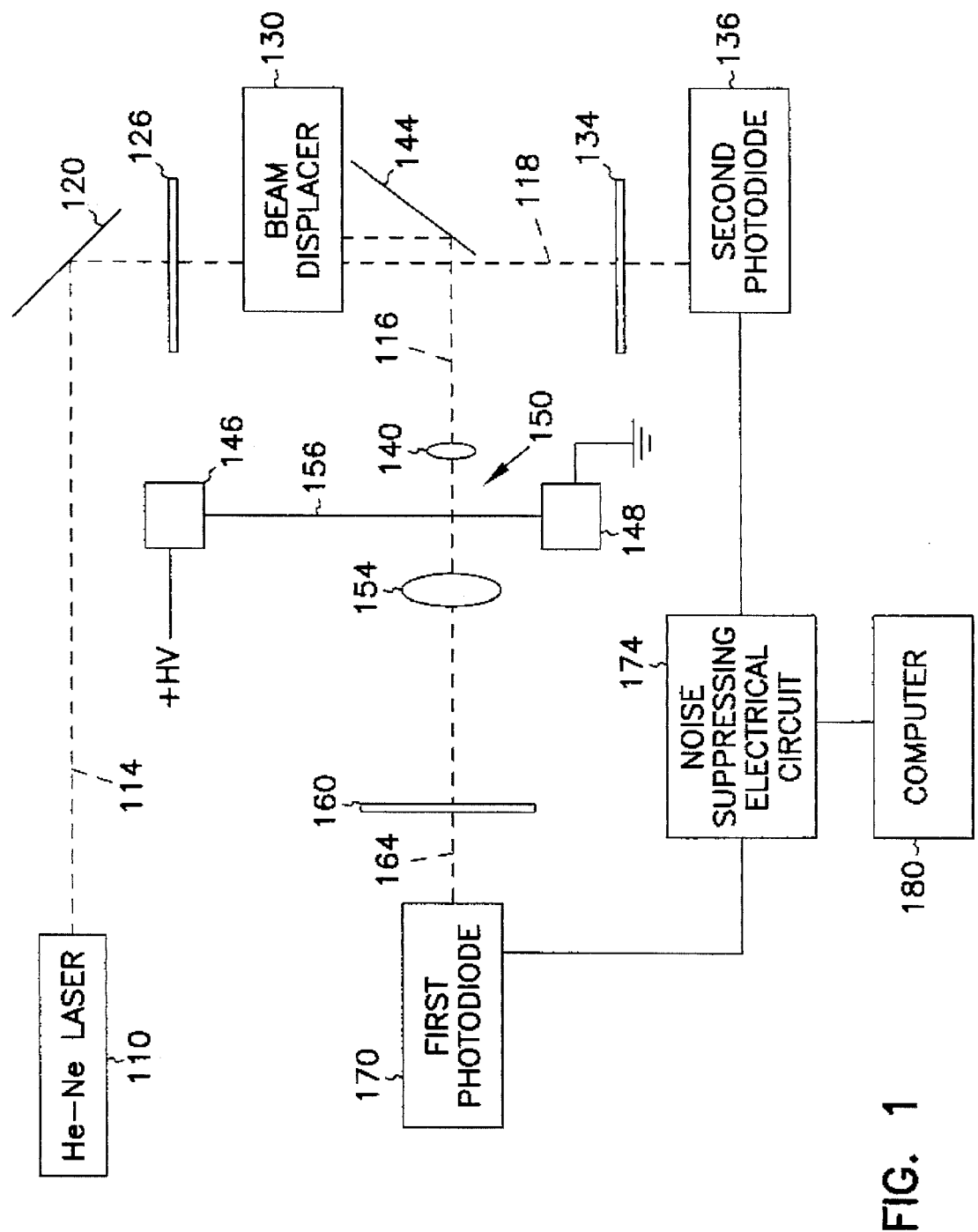
FIG. 1 is a schematic diagram of an embodiment of an on-column noise suppressing capillary separation system.

The present invention is a noise-suppressing capillary separation system (NSCSS) for detecting the real-time presence and/or concentration of an analyte in a sample. The present invention is also directed to a method of using the noise-suppressing capillary separation system to provide a real-time indication of the presence and/or concentration of an analyte in a sample. The NSCSS contains a capillary separation means such as a CE or LC system for the movement and separation of analytes. The presence and/or concentration of the analyte is detected by a detector at a detection zone near the exit end of the capillary.

The analyte can be detected by the present invention in "real time" and "on column" as the analyte passes through the capillary, i.e. any change of concentration of the analyte as it passes through the detection zone of the capillary can be detected essentially immediately without having to sample from the capillary for later analysis or signal average to reduce noise.

Laser energy is preferably used to provide a coherent light beam that is split into two: one as a reference beam and one as a sample beam for irradiating the analyte in the detection zone of the capillary. The absorbance of the analyte in the detection zone of the capillary is measured by a detector which has a noise suppressing electrical circuit.

I. Capillary Electrophoresis and Liquid Chromatography

As applied in the present invention, capillary electrophoresis system or liquid chromatography system that contains a capillary effective for use with a laser of suitable wavelength for detecting the analytes can be used. The present invention can be used with open-tube capillary electrophoresis as well as for capillary electrophoresis involving capillaries that contain separation-medium. Open tube capillary electrophoresis is useful in analyzing samples containing substances that have a tendency to plug a capillary with solid phase medium, for example, samples of cells, bacteria, or viruses. This invention is likewise suitable for use in liquid chromatography for noise suppression and improving detection limits. Capillary electrophoresis systems and liquid chromatography systems are well known in the art and are commercially available. As used herein, the term "capillary separation means" refers to a system that is either capillary electrophoresis (CE) or liquid chromatography (LC) wherein a capillary is used for separating analytes in a sample. Because the LC column in analytical LC is usually small in diameter, as used herein, the term "capillary" refers to a capillary in CE or a column in LC. Typically, such a capillary has an inside diameter of about 2 μm to 200 μm, more often about 14 μm to 100 μm.

In CE the capillary is preferably made of fused silica because fused silica is superior to other materials such as polymers and metals in permitting transmittance of coherent light of preferred wavelength in the UV region. In LC, even if the capillary is made of a nonsilica material, preferably at least the detection zone is made of fused silica or other materials which transmit UV radiation.

Interactions such as absorption of chromophores on the capillary wall can introduce noise. In cases wherein one chromophore is positively charged, the positively charged chromophore and negatively charged capillary wall may interact much more strongly than in the case of indirect anion detection. Therefore, coated capillaries are more favorable for indirect cation detection, especially when large molecules are used as chromophores. Coatings are commonly made with hydrophobic polymers. An example of an effective coating method is silation. Silation also reduces peak broadening of the eluting sample and long term drift. Methods of silating a fused silica capillary are well known in the art.

Typically, the outside surface of a fused silica capillary in CE is coated with a polyimide or polyamide. Near the exit end of the capillary, a detection zone can be created for the transmission of light by removing the polyimide or polyamide coating. The removal of the polyimide or polyamide coating can be accomplished by dipping the end of the polyimide or polyamide-coated fused silica capillary in concentrated sulfuric acid.

A. Direct Absorption Detection

An analyte containing a chromophore can be analyzed by eluting through a capillary in the CE or LC system. Before the chromophores reach the detection zone of the capillary, the transmitted light detected at the detection zone represents the background signal. As the chromophores pass by the detection zone, part of the irradiated laser radiation is absorbed by the chromophores. The transmitted light can be detected by the detector to determine the absorbance of the chromophores. The absorbance can be analyzed to obtain information on the presence and/or concentration of the chromophore, and therefore, of the analyte in the fluid passing through the detection zone. Representative suitable chromophores are color dyes such as malachite green which absorbs light of 633 nm wavelength. Other chromophores for absorbing light of other wavelengths are also known in the art.

The chromophores can be the analyte, or more commonly, the analytes are labeled, or tagged with a suitable chromophore before being injected into the capillary. Such labeling and tagging techniques are well-known in the art.

B. Indirect Absorption Detection

An analyte can also be detected without directly labeling or tagging before being injected into the capillary. A buffer with a chromophore can be passed through the capillary. When an analyte is injected into the capillary and reaches the detection zone, the interaction of the chromophore being transferred to (i.e. ion-pairing with) or being displaced by the analyte, thereby leading to a change in the absorbance of the fluid in the detection zone. The change in absorbance can be detected to determine the presence or concentration of the analyte.

For indirect absorption detection of anions, bromocresol green can be selected as the chromophore. Bromocresol green is soluble in water, very stable, and has a large molar absorptivity ($\epsilon = 7 \times 10^4$). A pH of about 8.8 it is almost completely disassociated. Bromocresol green also has little absorptive interaction with the capillary wall. Thus, this compound is suitable as a chromophore for indirect detection.

C. Collimation of Coherent Light in Capillary

In the analysis of the concentration of an analyte by absorbance measurement, the relation between the absorbance, the concentration of the analyte solution, and the light pathlength of the measuring device can be mathematically described. Preferably, the laser beam is directed to irradiate the capillary substantially orthogonally so that the beam passes through the diameter (i.e., the center) of the capillary.

However, in a capillary, if the diameter of the laser beam is not adequately small compared with the capillary inside diameter, the laser beam will pass through the solution inside the capillary with a distribution of pathlengths. The pathlength of the light in the beam can vary greatly depending on the position of the light in relation to the capillary. Such variations contribute to noise in the measurement of the absorbance of the analyte in the column.

As a result, the effective optical pathlength is much smaller than the inside diameter (i.d.) of the capillary. Further, part of the beam may be refracted by the wall of the capillary and is not detected by the detector. Lower light intensities due to poor collimation will lead to a lower signal-to-noise ratio. To reduce noise, it is therefore preferable to collimate substantially the whole light beam to irradiate through the axial center of the capillary. Generally, the laser beam directed to the capillary is collimated into the capillary with a beam diameter of less than about 0.25 of the insider diameter of the capillary. Preferably beam diameter is about 0.02 to about 0.25 times the insider diameter of the capillary.

It should be noted that although a He-Ne laser producing a coherent light of 632.8 nm was used in the preferred embodiment, such a laser is not essential and can be replaced by any source of coherent light with good pointing stability and suitable wavelength. By using UV lasers, one will be able to detect different kinds of analytes, especially proteins, nucleic acids and their constituents. Following the teaching of this invention, the selection of a laser of suitable wavelength and power can be accomplished following routine practices.

II. Noise Suppression Detector

Shot noise is the result of random current fluctuation of a statistical nature. When a photodetector is used for detecting light, the number of photons striking the photodetector in a specific time interval has a Poisson distribution, which leads to a variation of the current generated by the photodetector. A detector system that has eliminated all other noise except shot-noise is referred to herein as "shot-noise-limited."

Noise and spurious modulation in light can be suppressed or substantially eliminated from the data generated by a detector using photodetectors if a laser beam is split into a sample beam and a reference beam and the photocurrents generated by the two beams electronically subtracted one from the other.

In the preferred noise suppressing electrical circuit used in the present invention, a sample photodetector, preferably a photodiode, is used to generate a sample current when struck by light from the sample beam which is transmitted through the capillary. The sample current represents the composite of an informational signal impressed upon a carrier current. The carrier current represents a sample steady state signal modulated by noise. The sample steady state signal (as modulated by the noise) is represented by a sample steady state current.

A reference photodetector, preferably a photodiode, generates a reference current when struck by a reference beam. The reference current represents a reference steady state signal modulated by noise.

Current dividing means is provided for dividing the reference current into first and second components. The first component of the divided reference current includes a divided steady state signal which is preferably approximately equal in amplitude to the sample steady state signal of the sample current.

As a result, the first component of the divided current and the sample current are combined to reduce or, preferably, substantially cancel, the sample steady state signal of the sample current, thereby producing an output current indicative primarily of the informational signal of the sample current. In other words, one current (typically the first component of the divided reference current) is subtracted from the sample current to cancel out the sample steady state signal, thereby producing an output current which is free of what can be referred to as an output steady state signal. In those instances where the steady state signals are not cancelled out, the output current may contain an output steady state signal, i.e., the portion of the sample steady state signal not cancelled by the first component.

Although it is preferable that the reference current be larger than the sample current, the noise suppressing electrical circuit can also be used when the sample current is larger than the reference current. In that case, the sample current is divided into two components to cancel the sample steady state signal to obtain an output current which corresponds to the informational signal in the same manner as described above.

A. Optical Arrangement

A schematic diagram of one preferred double-beam laser absorption detector for CE is shown in FIG. 1. The light source is a 10 mW He-Ne laser 110 (GLG5261, NEC, Mountain Valley, Calif.), which operates at 632.8 nm. The laser beam 114 is split into a sample beam 116 and a reference beam 118. To split a laser beam this way, the laser beam 114 is reflected by a mirror 120 to direct the laser beam 114 through a polarizer 126, which polarizes the beam 114 into two separable components.

The polarized beam is then passed through a calcite beam displacer 130 (Karl Lambrecht Corp., Chicago, Ill.) to split the beam into orthogonally polarized sample and reference beams 116 and 118.

The polarizer 126 eliminates polarization noise, which can cause unsuppressible, uneven intensities in the calcite beam displacer 130. The calcite beam displacer presents different refractive indexes for the polarized light components, enabling them to travel in different paths. The calcite beam displacer 130 is rotated so that the reference beam 118 is made to be about twice as intense as the sample beam. Although such a method of splitting a laser beam is preferred, other means of splitting a laser beam, such as a half mirror, can also be employed.

The reference beam 116 is directed through a 5 mm diameter aperture 134 and strikes a photodiode 126, generating a reference photocurrent. The sample beam 116 is directed to a lens 140 by reflecting off a second mirror 144 (Newport). Lens 140, a 1-cm focal length quartz lens (Melles Griot Corp., Irvine, Calif.) is used to focus the laser beam 116 into a detection zone 150 made by removing a 5-mm section of polyamide coating from the fused-silica capillary 156 near the exit end of the capillary.

The inlet end of the capillary 156 is connected to a high voltage reservoir 146 and the exit end of the capillary 156 is connected to a grounded reservoir 148. The capillary 156 is preferably mounted on a precision x-y positioner (not shown) (Newport, 462 Series) for fine alignment of the capillary 156 in relation to the laser beam 116.

On the side of the capillary 156 opposite the side irradiated by the laser beam 116, light transmitted through the capillary detection zone 150 is focused by a 35-cm focal length quartz lens 154 (Melles Griot Corp.) and directed through a 5 mm diameter aperture 160. The laser beam 164 that passes through the aperture 160 is monitored by the sample photodiode (first photodiode) 170. The photocurrent generated at the reference photodiode (second photodiode) 136 and the sample photodiode 170 are directed to the noise suppressing electrical circuit 174, which is electronically connected to a computer 180 for analyzing the electrical data generated in the noise suppressing electrical circuit 174.

The apertures 134 and 160 isolate the sample beam 118 and the reference beam 116 from each other to avoid crosstalk, i.e., the light from one beam striking the photodiode intended for the other beam. The size and position of the apertures are carefully chosen to avoid vignetting, which is the result of part of the beam being blocked while the beam passes through the aperture. Vignetting causes noise if the beam moves.

The exact aperture size is determined based on variables within each system by simple experimentation. In one preferred method of determining aperture size, the capillary is aligned in relation with the laser beam to avoid Fabry-Perot fringes, which are interference patterns in the transmitted light. Vibrations in the capillary can change the alignment and introduce noise. Such vibration-caused noise can be substantially reduced by affixing the capillary on a solid mount and the detection zone of the capillary on an adjustable x-y positioner.

B. Noise Suppressing Electrical Circuit

Figure 2:
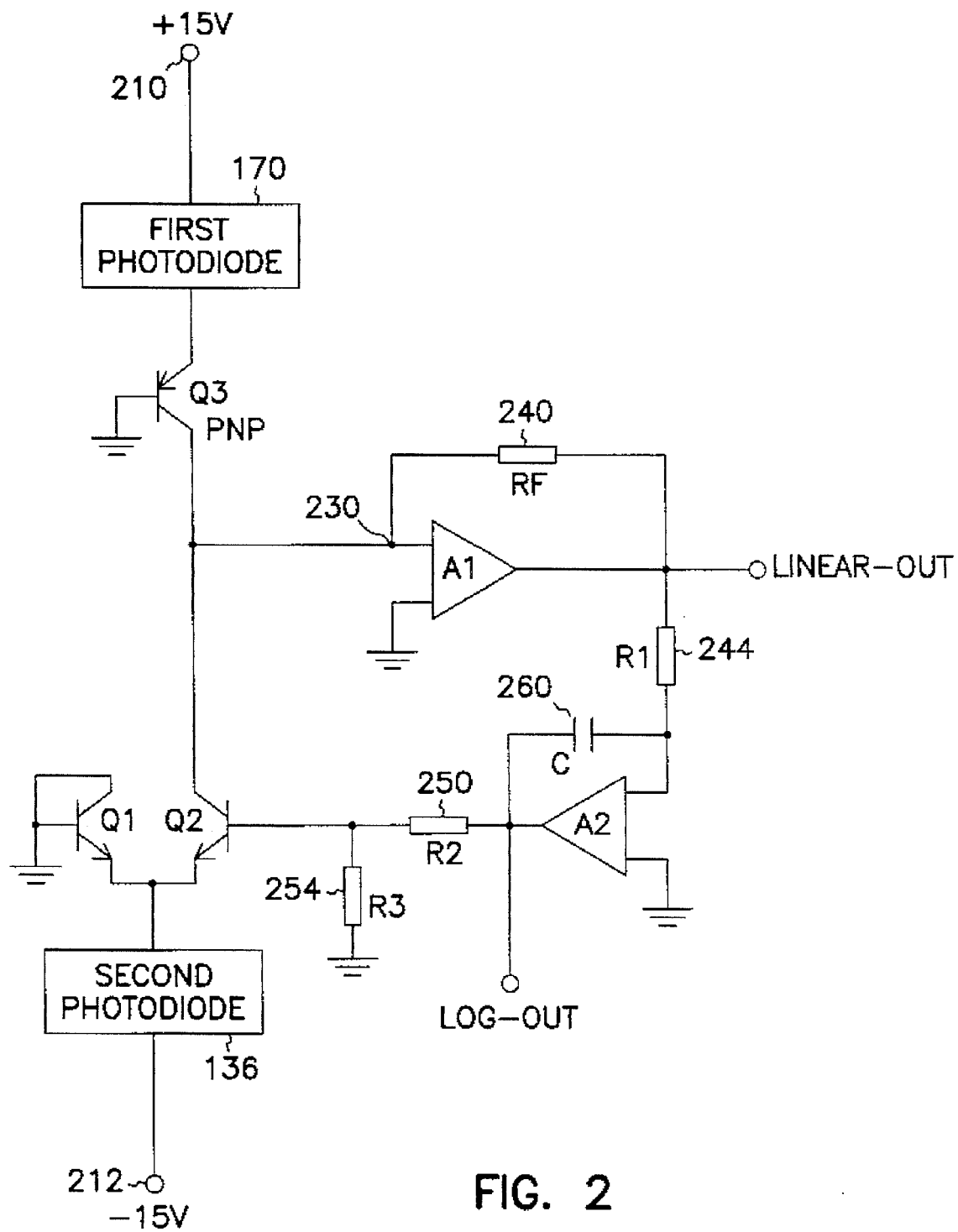
FIG. 2 is a schematic diagram for an embodiment of a noise suppressing electrical circuit.

One preferred noise suppression circuit used in the present invention is similar to those described by Hobbs et al., supra. FIG. 2 shows the schematic diagram of an embodiment of the noise suppression electronic circuit of the present invention. Two 12 v batteries 210 and 212 in series are used to drive the electrical circuit. Though power supplies can be used for powering the electrical circuit, preferably batteries are used because they tend to reduce noise in the circuit.

Two photodiodes 136 and 170 (BPW34, Siemens) serve as sample and reference beam detectors. The reference photodiode (second photodiode) 136 generates a reference steady state current when struck by the reference beam. The sample photodiode (first photodiode) 170 generates a sample current when struck by the transmitted light directed from the capillary detection zone. The sample current represents an informational signal modulating a steady state current. A PNP bipolar transistor $Q_3$ (2N3906) is used to prevent the capacitance of the sample photodiode 170 from loading the summing junction 230 of the operational amplifier, A1.

A pair of bipolar transistors (Q1,Q2) (Motorola MAT04), in a differential pair configuration, acts as a variable current divider. This current divider is electronically controlled to divide the reference current passed from reference beam photodiode 136 into two component currents. One of the two component currents, referred to as the first component, preferably has substantially the same steady state current amplitude as the steady state current amplitude of the sample current generated by the sample photodiode 170.

This first component current is subtracted from the sample current at the summing junction 230 of the operational amplifier A1 so that the steady state currents of the two substantially cancel out or at least reduce the steady state signal portion of the sample current, resulting in an output current that is substantially free of a component caused by excess noise, i.e., the steady state current of the output current at the summing junction is approximately zero. Preferably, the two currents have steady state amplitudes that are within 0.1% of each other, although any reductions in the steady state current portion of the output current are desirable.

The operational amplifier A1 (Motorola OP-27) converts the resulting output current at the summing junction 230 to a voltage. The operational amplifier A2 integrates the output voltage of A1 and feeds back to the differential pair Q1–Q2, which controls the division of the reference photocurrent. In the embodiment, $R_F$ is 20 KΩ, $R_1$ is 1 KΩ, $R_2$ is 1 KΩ, $R_3$ is 24 Ω, C is 2.2 microfarad. The circuit is shielded from the environment in the preferred embodiment by a piece of aluminum foil. Optionally, a ±15 V DC power supply (BK Precision, Model 1660, Chicago, Ill.) can be used to drive the noise suppressing electrical circuit.

III. Output from Noise Suppressing Capillary Separation System

The preferred noise suppressing electrical circuit has both a linear output, or linear-out (A1) and a log output, or log-out (A2).

A. Log Output

Log-out voltage, $V_{log}$ of A2 provides a low-pass filtered voltage related logarithmically to the sample and reference beam intensities (see Haller, K. L. and Hobbs, P. C. D. SPIE Proc., Feary, B. L., Ed., 1435, 298–309, 1991):

$$V_{log} = -\ln\left(\frac{i_{ref}}{i_{sig}} - 1\right)$$

Because the output from A2 is integrated, it typically contains less noise than the linear output at A1. The normalized transmittance is then $$\frac{I}{I_0} = \frac{\exp(-V_0) + 1}{\exp(-V) + 1}$$

where I is the intensity of the transmitted light through the capillary and $I_0$ is the transmitted light in the absence of absorption. V is the voltage registered from log-out in volts and $V_0$ is the log-out voltage in the absence of absorption. Since $V_0$ is set to be about −70 mV and V is small in a low concentration sample, the exponentials can be expanded to obtain:

$$\frac{I_0}{I} \cong \frac{2 - V}{2 - V_0} = 1 + \frac{\Delta V}{2 - V_0}$$

where $\Delta V = V_0 - V$ is the logout voltage change (i.e., peak height). Rearranging the equation, we obtain:

$$\frac{I_0}{I} - 1 = \frac{\Delta V}{2 - V_0}$$

Based on Beer's Law, the transmittance is:

$$\frac{I_0}{I} = 10^{\epsilon b c}$$

where ε is the molar absorptivity of the sample, b is the pathlength, c is the sample concentration, and k is a constant for a given reference beam and sample beam ratio.

For a low concentration sample, $I_0/I$ is about equal to 1 and thus, $$10^{\epsilon bc} \cong 1 + \epsilon bc \ln 10$$

Therefore, $$\epsilon bc \ln 10 = \frac{\Delta V}{2 - V_0}$$

Consequently, a relationship between the concentration of a sample and log-out voltage can be derived:

$$\Delta V = (2 - V_0) \ln 10 \, \epsilon bc = k \, \epsilon bc$$

where k is equal to $\{(2-V_0) \ln 10\}$. This equation provides an alternative for concentration calculations. A concentration versus peak height calibration curve for malachite green in a capillary separation system such as CE or LC can be constructed.

In the noise suppressing electrical circuit of the present invention as described hereinabove, the RMS noise density of the log-out voltage is:

$$\sigma V_{log} = (2)^{1/2}(\exp(V_{log}) + 1) \cdot \left(\frac{2q}{i_{sig}}\right)^{1/2} \cong 4\left(\frac{q}{i_{sig}}\right)^{1/2}$$

where q is the electron charge. In the NSCSS of the present invention, one can estimate the maximum log-out voltage within which the ratio of the collector currents of the two transistors, $Q_1$ and $Q_2$, is dependent on the difference voltage $\Delta V_{BE} = V_{BE2} - V_{BE1}$. The ratio of the collector currents for the two transistors can be expressed as:

$$\frac{I_{C2}}{I_{C1}} = \exp\left(\frac{V_{BE2} - V_{BE1}}{V_T}\right) = \exp\left(\frac{\Delta V_{BE}}{V_T}\right)$$

where $I_{C2}$, $I_{C1}$ are the collect currents in $Q_2$ and $Q_1$ and $V_T$ is the thermal voltage ($=kT/q \cong 26$ mV at 300° K., where q is the electron charge).

$$I_{C1} = \frac{\alpha_F I_{ref}}{1 + \exp\left(\frac{V_{BE}}{V_T}\right)}$$

$$I_{C2} = \frac{\alpha_F I_{ref}}{1 + \exp\left(\frac{-V_{BE}}{V_T}\right)}$$

where $\alpha_F$ ($\approx 1$) is the ratio of emitter to collector current with the transistor operating under forward bias and $I_{ref}$ is the reference photodiode current. When $|\Delta V_{BE}| > 4V_T$, the collector currents become practically independent of the voltage difference $\Delta V_{BE}$; their value being zero or $\alpha_F I_{ref}$. The most significant difference between ideal and real transistors is the presence of finite spreading resistances. Assuming the transistors are ideal, the maximum change of $\Delta V_{BE}$ would be from $-4V_T$ to $+4V_T$. For $\Delta V_{BE} = \pm 4V_T = \pm 104$ mV, $$V_{max} = \frac{R_2 + R_3}{R_3} \Delta V_{BE} = \pm \frac{1000 + 24}{24} \times 104 \text{ mV} = \pm 4.4 \text{ V}$$

Therefore, the maximum change of $V_{log}$ is 8.8 V. However, the differential transistors behave in an approximately linear fashion only if difference voltages $\Delta V_{BE}$ less than approximately $\pm 26$ mV, which corresponds to:

$$V_{log} = \pm 26 \text{ mV} \frac{1024}{24} = \pm 1.1 \text{ V}$$

The noise-to-signal ratio can be expressed as:

$$\frac{N}{S} = \frac{d\Delta V_{log}}{2|V_{max}|}$$

where $d\Delta V_{log}$ is log-out voltage noise. For a 20-µV noise level in the log-out voltage, the noise to signal ratio is $$\frac{N}{S} = \frac{20 \times 10^{-6} \text{ V}}{8.8 \text{ V}} = 2.3 \times 10^{-6}$$

Rearranging equation 8, the absorbance noise becomes $$dA = \frac{d\Delta V}{(2 - V_0) \ln 10}$$

For a 20-µV noise, $$dA = \frac{20 \times 10^{-6} \text{ V}}{(2 - 0.1) \ln 10} = 4.3 \times 10^{-6}$$

From eq. (13) and (14), we obtain:

$$\frac{d\Delta V_{log}}{2|V_{max}|} \cong \frac{dA}{2}$$

$$dA \cong \frac{d\Delta V_{log}}{|V_{max}|}$$

This equation can be used to estimate the detection limit in the log-out mode.

A more accurate expression relating the change in log-out voltage ($\Delta V$) and the sample concentration can also be derived:

$$\Delta V = \left(2 - \frac{V_0}{|V_T|\left(\frac{R_2 + R_3}{R_3}\right)}\right) |V_T| \left(\frac{R_2 + R_3}{R_3}\right) \ln 10 \, \epsilon bc$$

$$= \left(2 - \frac{4V_0}{|V_{max}|}\right) \frac{|V_{max}|}{4} \ln 10 \, \epsilon bc$$

Rearranging the equation we obtain:

$$\frac{\Delta V}{|V_{max}|} = \left(\frac{1}{2} - \frac{V_0}{|V_{max}|}\right) \ln 10 \, \epsilon bc$$

So, $$\frac{d\Delta V_{log}}{|V_{max}|} = \left(\frac{1}{2} - \frac{V_0}{|V_{max}|}\right) \ln 10 \, dA$$

$$\cong \frac{\ln 10}{2} dA, \text{ since } v_0 \ll |V_{max}|$$

Therefore, $$dA \cong \frac{d\Delta V_{log}}{|V_{max}|} \frac{2}{\ln 10}$$

The major factors determining the detection limits are the concentration of the chromophore (CM); the dynamic reserve (DR)=(A/ΔA), which is the ratio of the background absorbance to the absorbance noise; and the transfer ratio (TR), which is the number of chromophore molecules transferred or displaced by one analyte. The minimum detectable concentration at the detector is determined by the following equation:

$$C_{LOD}=(C_M/TR) \cdot DR$$

(Yeung, E. S.; Kuhr, W. G. *Anal. Chem.*, 63, 275A–282A, 1991).

These parameters are not independent. As $C_M$ decreases, DR may decrease. Equilibrium and surface effects can further reduce TR.

With further development of equation (20) based on Beer's Law, we obtain:

$$C_{LOD} = \left(\frac{1}{TR}\right) \frac{\Delta A}{\epsilon b}$$

Based on equation (8), the following expression is derived:

$$d\Delta V_{log} = k d A$$

Therefore, $$d\Delta V_{log} = k d A$$

Therefore, $$C_{LOD} = \frac{1}{TR} \frac{d\Delta V_{log}}{k \epsilon b}$$

where $d\Delta V_{log}$ is the log output noise in the noise suppressing electrical circuit, and $\epsilon$ is the absorptivity of the sample.

B. Linear Output

The linear output from A1 is a first derivative of the sample current. Using this derivative signal, minor spectral features can be detected, which is particularly advantageous when two peaks are partially overlapped because peak overlaps are common in CE or LE separation for complex mixtures. Theoretically, the RMS current noise $i_{ns}$ of the sample photocurrent $i_{sig}$ is then:

$$i_{ns} = (2 q i_{sig})^{1/2}$$

where q is the electron charge ($1.6 \times 10^{-19}$ coulomb). Converting to voltage and time, considering shot-noise in the reference beam and the sampling bandwidth, the linear output voltage noise is:

$$V_{ns} = i_{ns} \cdot R_f (2 \Delta f)^{1/2}$$

where $R_f$ if the feedback resistance and $\Delta f$ is the bandwidth.

Whether using the log output or the linear output, the noise suppression electrical circuit according to the present invention is useful for reducing noise without the corresponding need to carefully match electronic components found in conventional noise suppression systems. The only requirements are a matched differential pair, a large collector coefficient B, and operation in the active region. As long as each of the photodiodes is in the linear response range, the photodiodes do not even have to be matched. There is also no need for careful tuning of the electronics because the negative feedback can be applied to keep the net DC photocurrent at zero to result in noise cancellation and shot-noise limited performance.

Likewise, signal averaging and multiple scans, typically used to reduce noise in conventional systems, are not needed. Noise can typically be suppressed to 10 times the shot-noise-limited level without signal-averaging when using the NSCSS of the present invention. If desired, however, signal-averaging can be performed electronically or manually by averaging data from multiple measurements in the application of the present invention, such signal-averaging is not necessary to realize the noise suppression benefits of the invention.

Using the direct absorption CE method of the present invention, an analyte can be detected at a concentration that is about 10 to about 100 times the analyte concentration that is shot-noise-limited, typically in the range of about $10^{-8}$M to about $10^{-7}$M.

Indirect absorption CE is useful for detecting analytes in small samples. For example, in the analysis of single cells, there is often a limited supply of sample. The increased sensitivity of the NSCSS can be advantageously utilized to detect small samples in a capillary with a small i.d. Using the present invention in indirect absorption in CE, an analyte can be detected at a concentration that is about 20 to about 200 times the analyte concentration that is shot-noise-limited, typically in the range of about $10^{-7}$M to about $10^{-6}$M. Likewise, in LC, by applying the present invention, the sensitivity of detecting an analyte is also increased compared to conventional detection systems.

The detection limit is inversely proportional to the capillary inside diameter. Even with capillaries as small as about 20 μm in inside diameter, using a laser beam diameter of about 10 μm, there is little alignment noise. On the other hand, the sensitivity in commercially available detectors deteriorates much faster with the decrease of capillary diameter. With commercial systems, a capillary smaller than 50 μm i.d. does not usually provide good sensitivity.

In the NSCSS of the present invention, the collimated laser beam can easily be focused down to a spot of a few micrometers. In this way, almost all of the light passes through the inside core of the capillary along a diameter and Beer's Law will hold, resulting in low noise compared to commercial systems. This is true for capillaries in the NSCSS of as small as 20 μm i.d. or less.

EXAMPLES

To illustrate the practice of the present invention, examples of preferred embodiments are presented below. The examples are illustrative only and should not be construed as limiting the invention, which is defined by the claims appended hereto.

In runs conducted in a commercial system for comparison with the NSCSS of the present invention, all operational parameters were identical for both the NSCSS and the commercial system, except for the effective length of the capillary. In the NSCSS, the output voltage from either linear-out or log-out of the noise suppressing electrical circuit was sent to a data acquisition system, consisting of an IBM PC compatible computer equipped with an A/D board (Chromperfect, Justice Innovation, Palo Alto, Calif.) for data analysis.

The buffer used for running the CE (running buffer) consisted of, essentially, 10 mM disodium phosphate (certified ACS grade, Fisher, Fair Lawn, N.J.), adjusted to pH 7.5 using phosphoric acid. Malachite green was obtained from Exciton, Inc. (Dayton, Ohio) and bromothymol blue from J. T. Baker (Phillipsburg, N.J.). The water used was purified with a commercial system (Millipore Corp., Milford, Mass.). Samples were diluted by using the running buffer. All solutions and the buffers were filtered with 0.22 μm cutoff cellulose acetate filters (Alltech Associates, Inc., Deerfield, Ill.) before use. This filtration step greatly reduced noise spikes caused by particles passing through the detection zone of the capillary.

EXAMPLE 1

CE Direct Absorption Analysis of Malachite Green

The above-mentioned noise suppression detector with the noise suppressing electrical circuit (shown in FIG. 2) and optical system (shown in FIG. 1) were used to determine ten different concentrations (from $2\times10^{-8}$M to $8\times10^{-6}$M) of malachite green. For low voltage measurements, a voltmeter (Keithley, Model 177) was connected between the noise suppressing electrical circuit and the A/D board to provide 100× gain. Data were acquired five times a second. The capillary was a 54 cm long, 75 μm i.d. and 360 μm o.d. fused-silica capillary (Polymicro Technologies, Inc., Phoenix, Ariz.). The effective length (i.e. the length of the capillary before the detection zone) of the capillary was 45 cm. A high-voltage power supply (Glassman, Whitehouse Station, N.J.) was used to apply +18 kV across the capillary. Before the injection of samples, the capillary was flushed with aqueous 0.1M NaOH overnight, followed by the running buffer for about 4 hours. The running buffer was 10 mM phosphate buffer at pH 7.5. Injections were made electrokinetically at the positive end at 5 kV for 5 seconds or hydrodynamically by lifting the sample reservoir 10 cm above the grounded buffer for 7 seconds.

Figure 3:
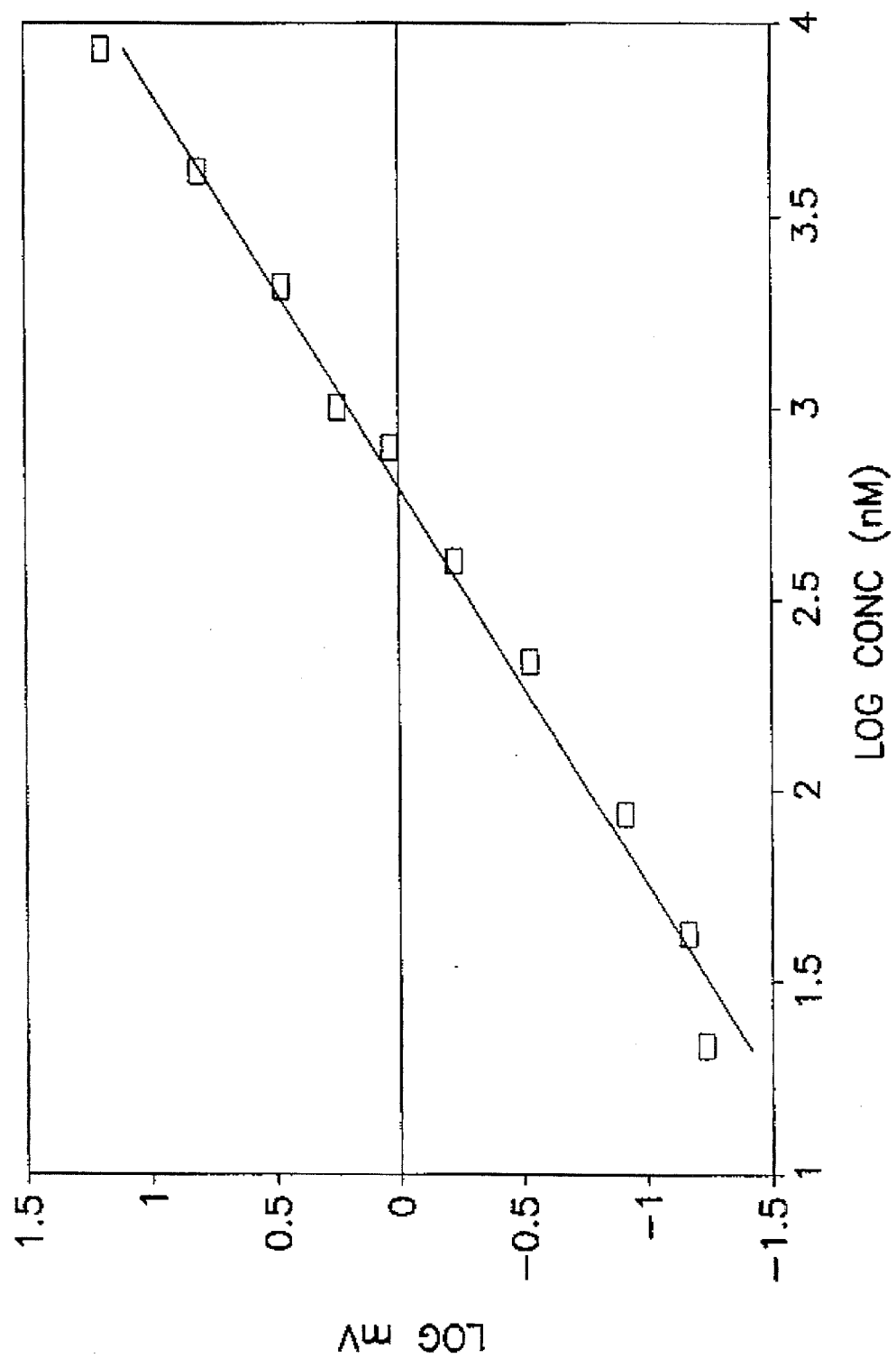
FIG. 3 is a graph of log (log-out voltage) vs. log (malachite green concentration) in an embodiment using NSCSS of the present invention.

FIG. 3 is a graph of log (log-out voltage peak height) versus log (malachite green concentration). The data from three consecutive injections were averaged into each voltage peak height. It was found that over 3 orders of magnitude, the voltage peak height was linearly related to the sample concentration. The correlation coefficient ($r^2$) for linear regression was 0.994. The curve shows good linearity. The slope for this curve was 0.943 with a correlation coefficient $r^2$=0.989.

According to equation (8), the theoretical detection limit for malachite green ($\epsilon=7.5\times10^4$ measured as dissolved in the running buffer) is $6.2\times10^{10}$M at the detection zone. In the NSCSS of the present invention, with careful alignment, collimation, laser stabilization and noise suppression, a 49-μV change was measured for $2\times10^{-8}$M malachite green injected. This voltage was approximately the same as the predicted value based on equation (8), 52 μV.

EXAMPLE 2

Separation of Bromothymol Blue and Malachite Green with NSCSS

The NSCSS of the present invention of Example 1 was used for detecting bromothymol blue ($2\times10^{-6}$M) in a sample. The operational conditions are similar to those of Example 1. The result shows that the baseline was stable and the peaks were sharp. The number of theoretical plates was calculated to be $4.5\times10^4$ for malachite green and $3\times10^4$ for bromothymol blue. These theoretical plate numbers are reasonable for CE operations.

EXAMPLE 3

Comparison of NSCSS with Commercial Systems

The NSCSS of the present invention of Example 1 was compared with commercial CE systems under the same operational conditions. For absorbance comparisons, a Model 3140 CE system (Isco, Inc., Lincoln, Nebr.) and a Spectraphoresis CE system (Spectra Physics, Mountain View, Calif., Model 1000) operating at an absorption wavelength of 633 nm were used. In the commercial system, a 75 μm i.d., 360 μm outside diameter (o.d.) capillary with 67 cm total length and 60 cm effective length was used. The running potential (i.e. the voltage for separating the ions in CE) applied across the capillary was +25 kV. The operation of the CE and detector systems according to the present invention were as previously described.

The detectability of the NSCSS of the present invention was found to be 25 times better than that for the commercial detectors. The electropherograms were obtained for analyte concentrations that produced a barely discernible peak at roughly twice the peak-to-peak noise.

Figure 4:
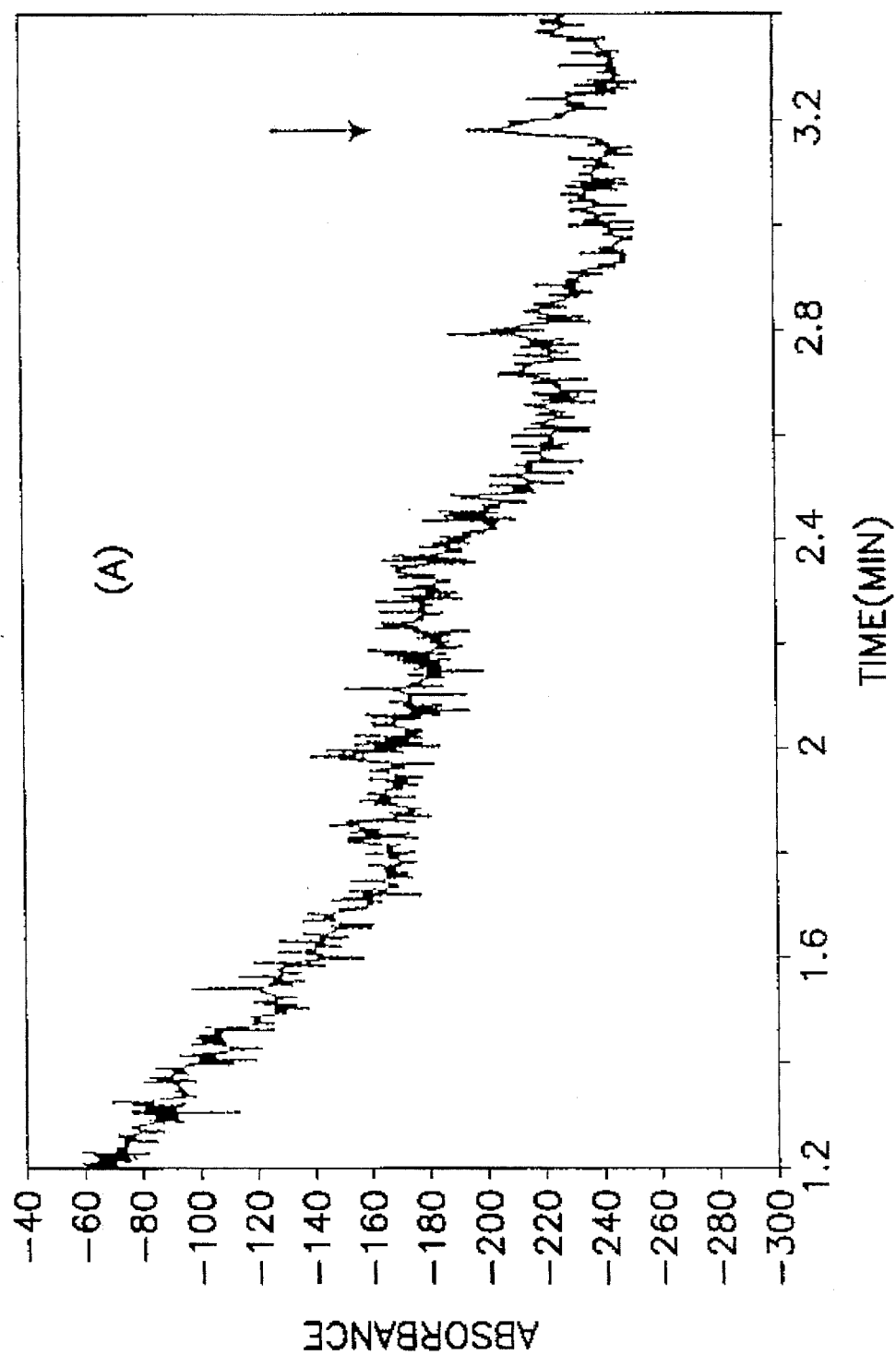
FIG. 4 is a graph of the absorbance data obtained in the analysis of $5 \times 10^{-7}$ malachite green in a commercial CE system.

FIG. 4 is a graph of the absorbance versus time data obtained in the analysis of $5\times10^{-7}$M malachite green in the commercial Spectra Physics instrument. The signal-to-noise ratio was about 2. With the commercial Isco instrument, the same signal to noise ratio was observed for an injected malachite green concentration of $2\times10^{-6}$M.

Figure 5:
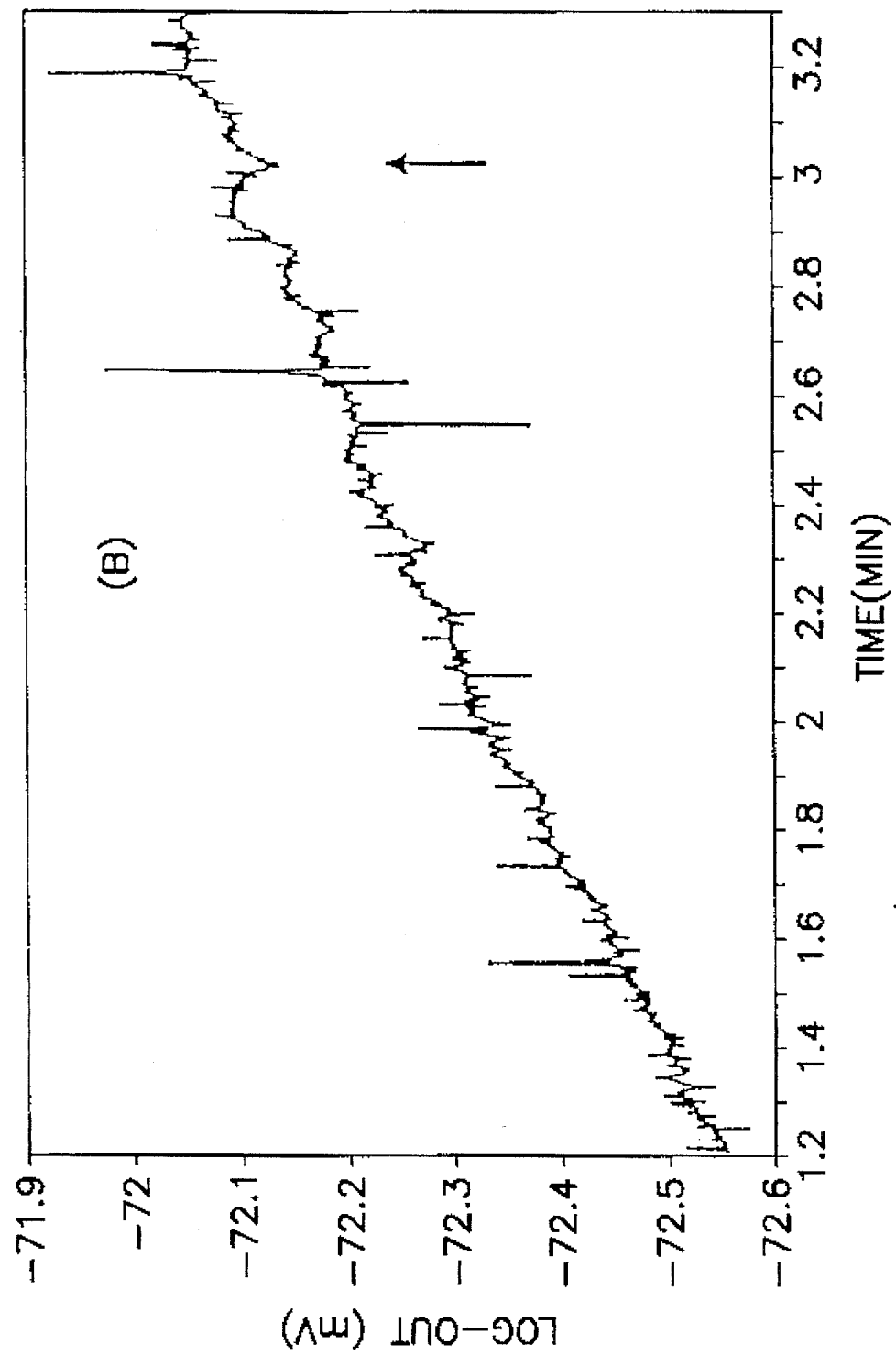
FIG. 5 is a graph of the log-out voltage data obtained in the analysis of $2 \times 10^{-8}$ malachite green in a NSCSS of the present invention.

FIG. 5 is a graph of the log-out voltage versus time data obtained using the NSCSS of the present invention. A peak (see arrow) can still be seen for a $2\times10^{-8}$M injected malachite green concentration. Data show that the NSCSS of the present invention has a 25-fold improvement of the detection limit over the best commercial CE systems presently available.

Figure 6:
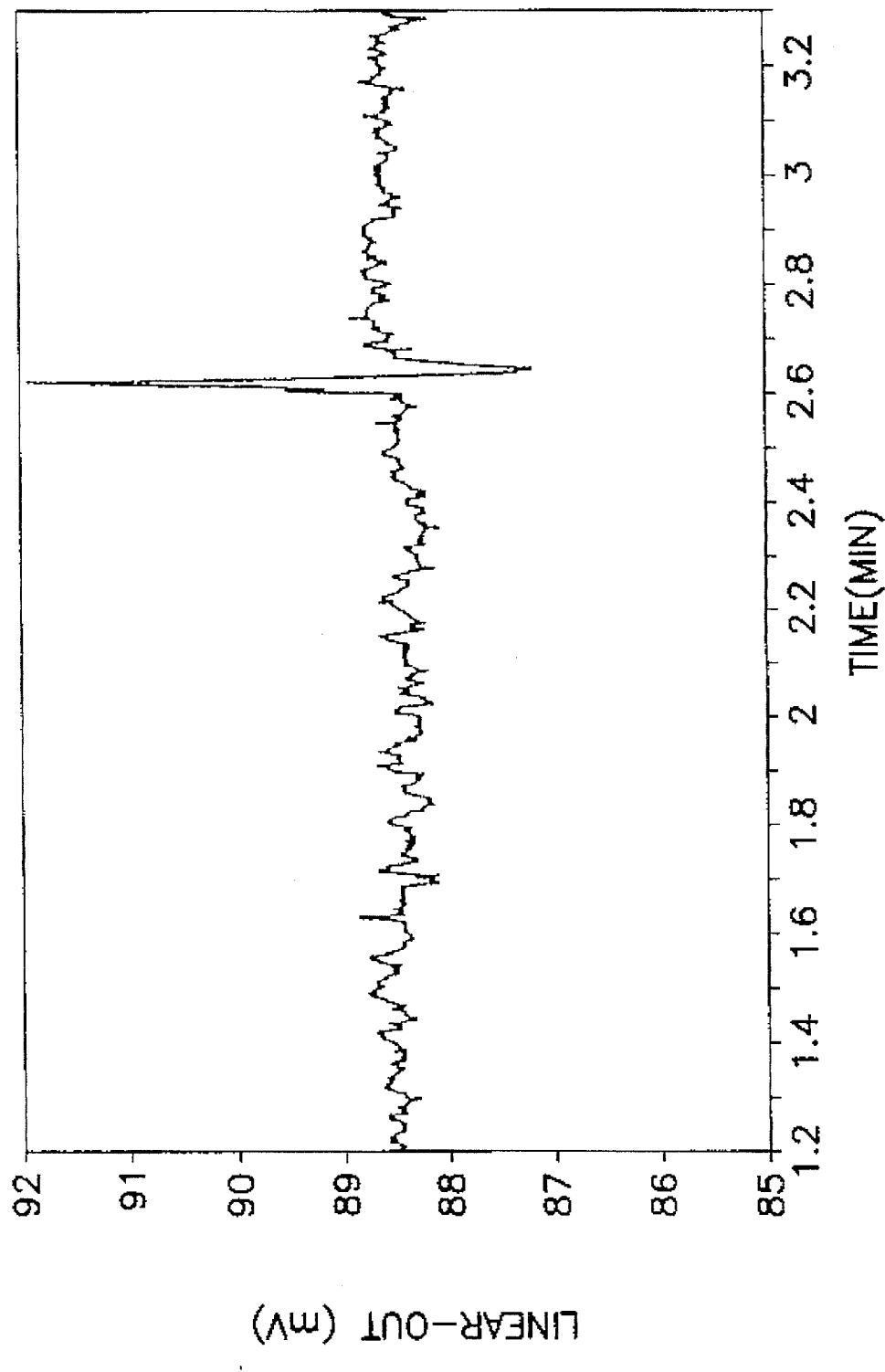
FIG. 6 is a graph showing the linear-out voltage data obtained in the analysis of $4 \times 10^{-7}$ malachite green in a NSCSS of the present invention.

FIG. 6 is a graph of the linear-out voltage versus time data obtained using the NSCSS of the present invention. The linear-out from the noise suppressing electrical circuit was amplified 100× by a voltmeter before A/D conversion. For $4\times10^{-7}$M malachite green injected, a derivative peak can be clearly seen. The corresponding detection limit is below $1\times10^{-7}$M, which is 5 times better than that of the commercial CE systems.

EXAMPLE 4

Anion Indirect Detection, 75 μm i.d. Capillary

The NSCSS for this example was essentially the same as that described in EXAMPLE 1. In indirect detection, the laser beam was split by passing through a polarizer and a Wollaston prism. A 1 cm focal length quartz lens (Melles Griot, Irvine, Calif.) was used to focus the laser beam (about 5 μm diameter) into the detection window of the 75 μm i.d. capillary. At an angle of 180° to the incident beam, the transmitted light from the capillary was collected by a 35 cm focal length quartz lens, and directed onto the sample photodiode. The output voltage from the log output was amplified 10× by a voltmeter (Keithley, Model 177) and sent to an IBM PC/AT computer. Data was acquired five times a second via a 24-bit A/D conversion interface (ChromPerfect Direct, Justice Innovations, Palo Alto, Calif.).

A high-voltage power supply (Glassman High Voltage, Inc., Whitehouse Station, N.J.) was used to apply 15 kV across the capillary. Injections were performed electrokinetically at the positive end at 15 kV for 2 seconds.

For absorbance comparison, a commercially available system, Spectra Physics CE (Spectra Physics, Mountain View, Calif., Model 1000) operating at 633 nm was used. Except for the effective length of the capillary and the applied voltage, all other operational parameters were identical for both the double-beam indirect laser absorption detection and the commercial system.

Fused silica capillaries of 75 μm i.d., 360 μm o.d. (PolyMicro Technologies, Inc., Phoenix, Ariz.) were used for the NSCSS of the present invention and in the commercial system. The capillaries were flushed with aqueous 0.1M NaOH for 6 hours, followed by equilibration with the running buffer for 6 hours before sample injection.

The separation buffer for anions was composed of 0.5 mM bromocresol green (J. T. Baker, Phillipsburg, N.J.). The pH was adjusted to 8.8 by 0.1M NaOH. Water was deionized with a water purification system (Millipore Corp., Milford, Mass.). All solutions and the buffer were filtered with 0.22 μm cutoff cellulose acetate filters before use.

Figure 7:
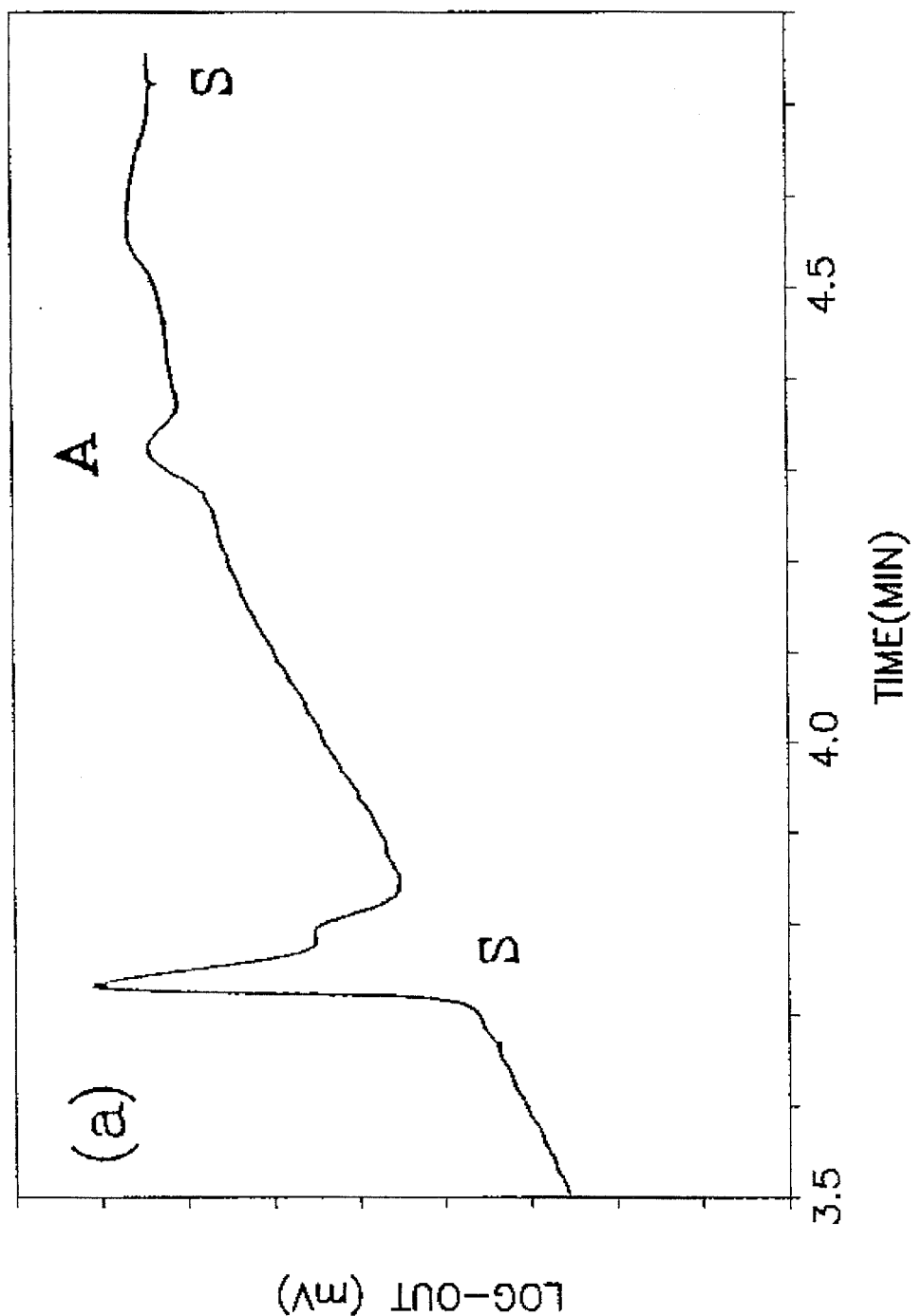
FIG. 7 is a graph of the log-out voltage versus time data of indirect absorption detection by analysis of $1.5 \times 10^{-7}$M pyruvic acid sodium salt in CE with a capillary of 75 μm i.d. using a NSCSS of the present invention.

Four different injected concentrations from $1.5\times10^{-5}$M to $1.5\times10^{-7}$M of pyruvic acid sodium salt (Aldrich, Milwaukee, Wis.) were studied using a 75 μm i.d. capillary of 36 cm length, 30 cm effective length. Each data point was an average of peak areas for three consecutive injections. Over 2 orders of magnitude, the peak areas were linearly related to the sample concentrations. The log-log graph gives a slope of 0.88 and a correlation coefficient ($r^2$) of 0.999. FIG. 7 is a graph of the log-out voltage versus time data obtained by analysis of $1.5\times10^{-7}$M pyruvic acid sodium salt. In FIG. 7,(A) represents the pyruvate anion peak, and the peaks denoted (S) represent the system peaks. A 0.48 mV peak for the pyruvic anion can be seen. The noise of 0.16 mV is equivalent to $5\times10^{-8}$M pyruvate injected. The theoretical detection limit if Beer's Law is followed is $C_{LOD}=7\times10^{-8}$M. The similarity of the operational and theoretical results show that in the NSCSS of the present invention, collimation permits the use of the full internal diameter of the capillary as the optical pathlength.

Figure 8:
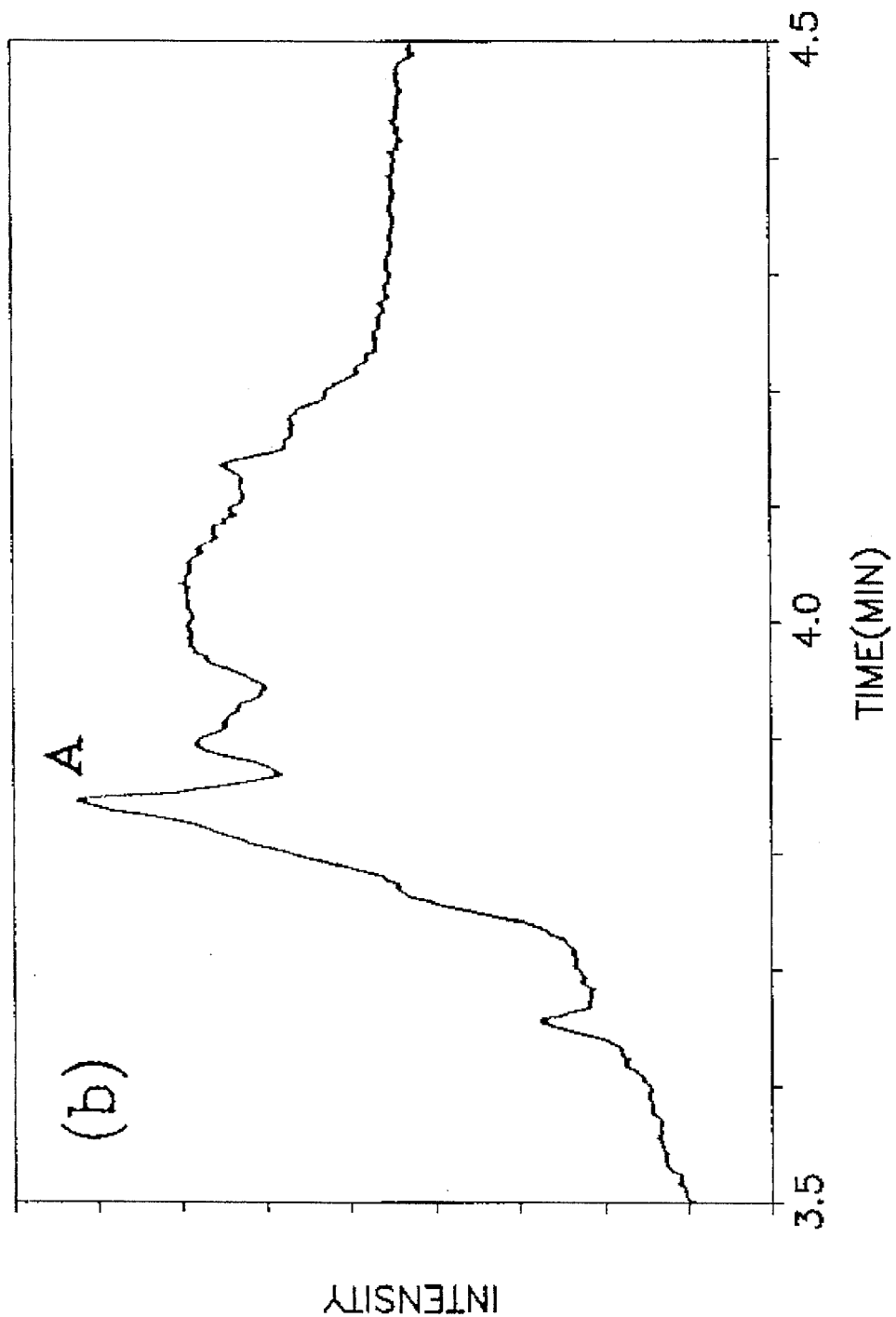
FIG. 8 is a graph of the transmitted light intensity versus time data of indirect absorption detection in the analysis of $1.5 \times 10^{-6}$M pyruvic acid sodium salt in CE with a capillary of 75 μm i.d. using a commercial system.

FIG. 8 is a graph of the intensity of transmitted light result versus time obtained in analysis of $1.5\times10^{-6}$M pyruvic acid sodium salt using the best presently available commercial system (Spectra Physics instrument), under the same conditions as the run of FIG. 7. For this commercial system, a capillary of 43 cm length, 35 cm effective length was used under 20 kV voltage. In FIG. 8,(A), the pyruvate anion peak, shows that the signal-to-noise ratio was about 2. Comparison shows that the NSCSS of the present invention achieved better than the 15-fold improvement on the detection limit over the best commercial system.

EXAMPLE 5

Anion Indirect Detection, 14 μm Capillary

Runs were conducted in a manner analogous to that of Example 4 using capillaries of 50 cm total length, 39 cm effective length, 14 μm i.d., 360 μm o.d. (PolyMicro Technologies, Inc., Phoenix, Ariz.) for both the NSCSS of the present invention and for the commercial system (Spectra Physics instrument). A 20× microscope objective (Edmund Scientific, Barrington, N.J.) was used for focusing the laser beam onto the capillary in the NSCSS of the present invention. Injections were performed hydrodynamically by lifting the sample reservoir 15 cm above the grounded buffer reservoir for 15 seconds.

Figure 9:
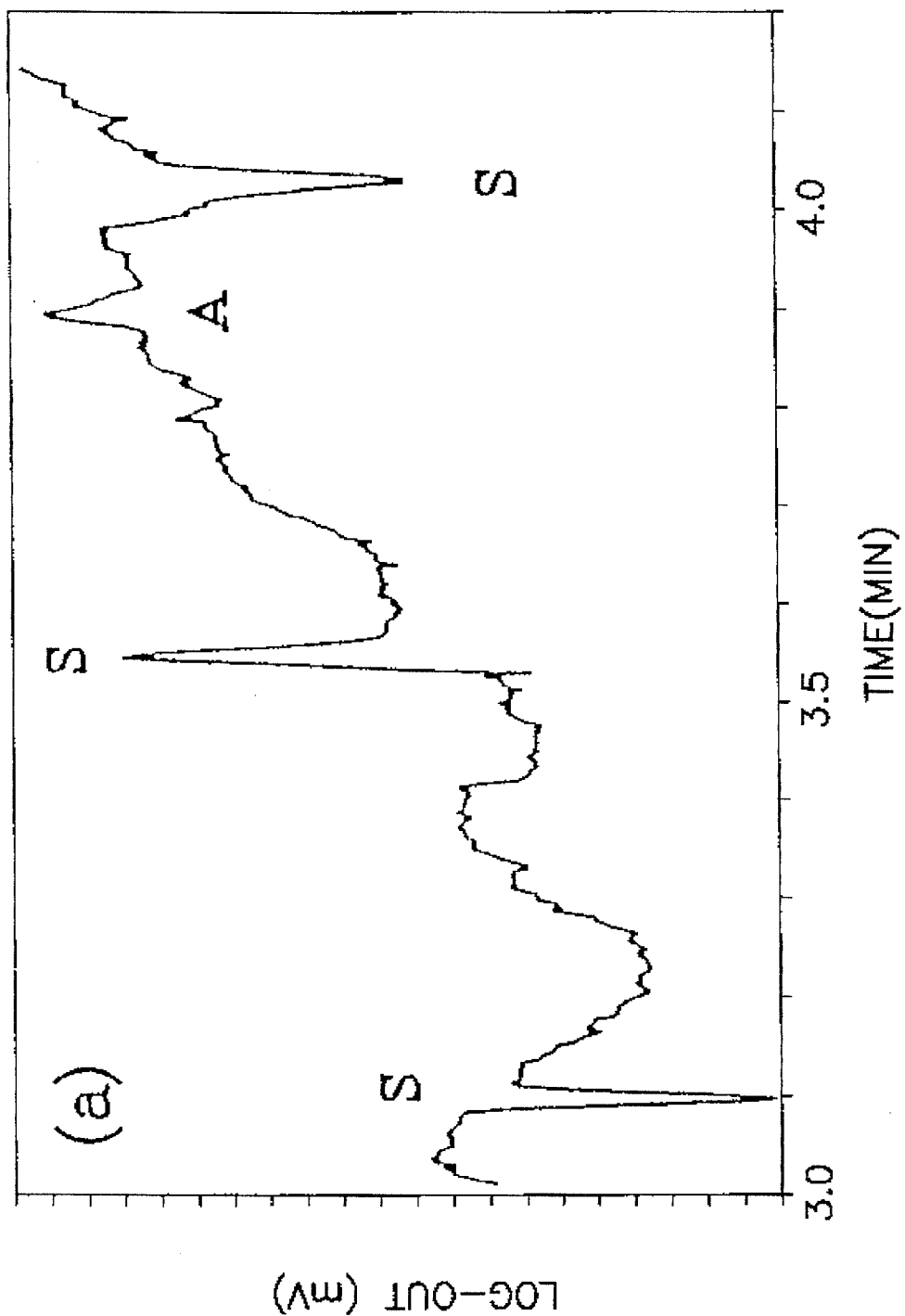
FIG. 9 is a graph of the log-out voltage versus time data of indirect absorption detection in the analysis of $6 \times 10^{-6}$M pyruvic acid sodium salt in CE with a capillary of 14 μm i.d. using a NSCSS of the present invention.

Six different sample concentrations from $1.2\times10^{-4}$M to $6\times10^{-6}$M were studied. Each data point was an average of the peak areas of three consecutive injections. The peak areas were linearly related to the sample concentrations. FIG. 9 shows the log-out voltage of the analysis of $6\times10^{-6}$M pyruvate using a NSCSS of the present invention. Peak (A) represents the pyruvate anion peak, and the peaks denoted by (S) represent the system peaks. Peak (A) is a small peak, but can clearly be seen. The detection limit is about $3\times10^{-6}$M.

Figure 10:
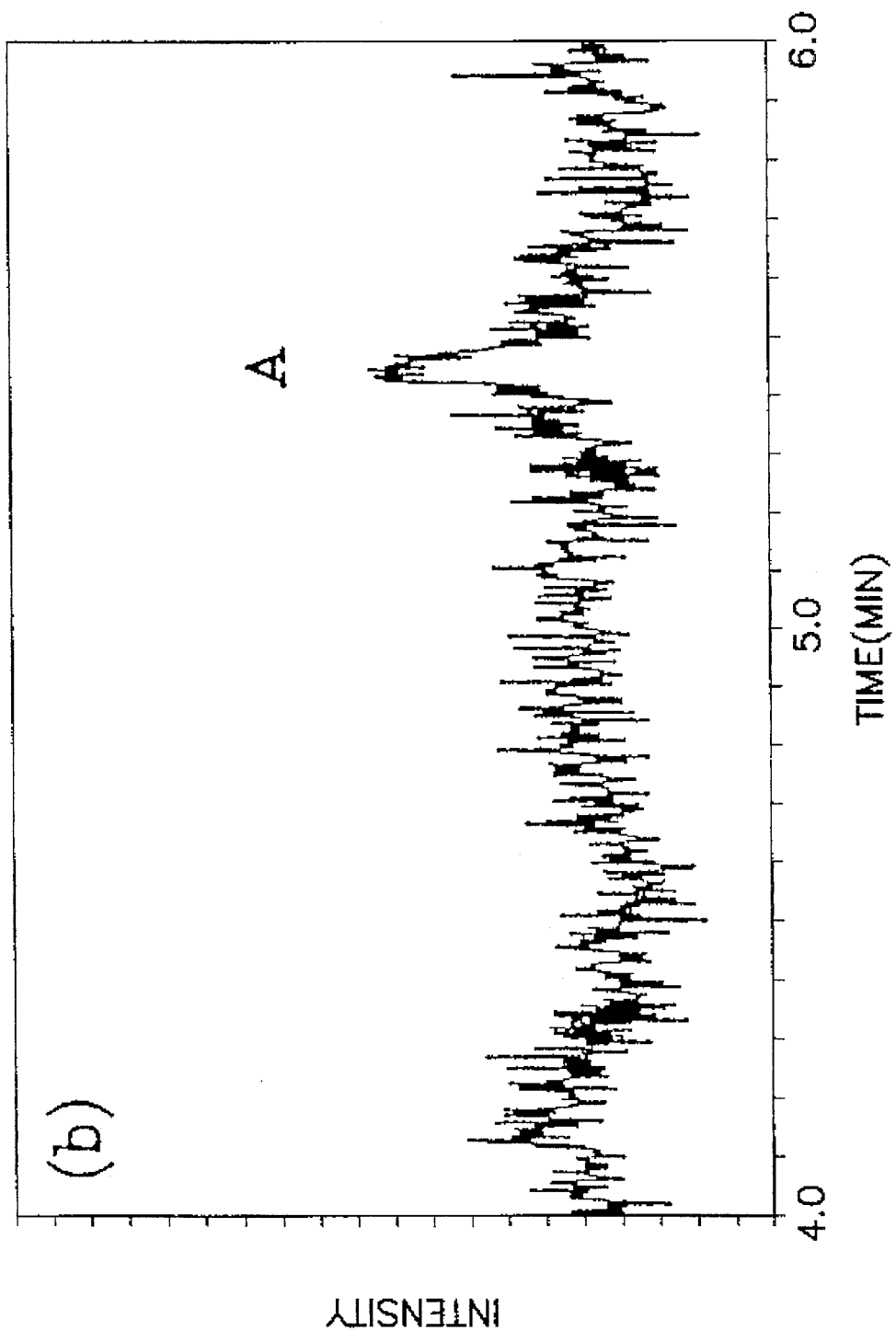
FIG. 10 is a graph of the transmitted light intensity versus time data of indirect absorption detection in the analysis of $3 \times 10^{-4}$M pyruvic acid sodium salt in CE with a capillary of 14 μm i.d. using a commercial system.

FIG. 10 is a graph of the intensity of transmitted light versus time data using a commercial detector. A represents the pyruvate anion peak. The NSCSS of the present invention had a 100-fold improvement in performance over the commercial system.

EXAMPLE 6

Detection of Cation by Indirect Absorption Detection

Runs were conducted in a manner analogous to that of Example 4. A 40 cm total length, 33 cm effective length capillary of 75 μm i.d. and 14 μm i.d. capillaries in a manner analogous to that in Example 4 and Example 5.

Figure 11:
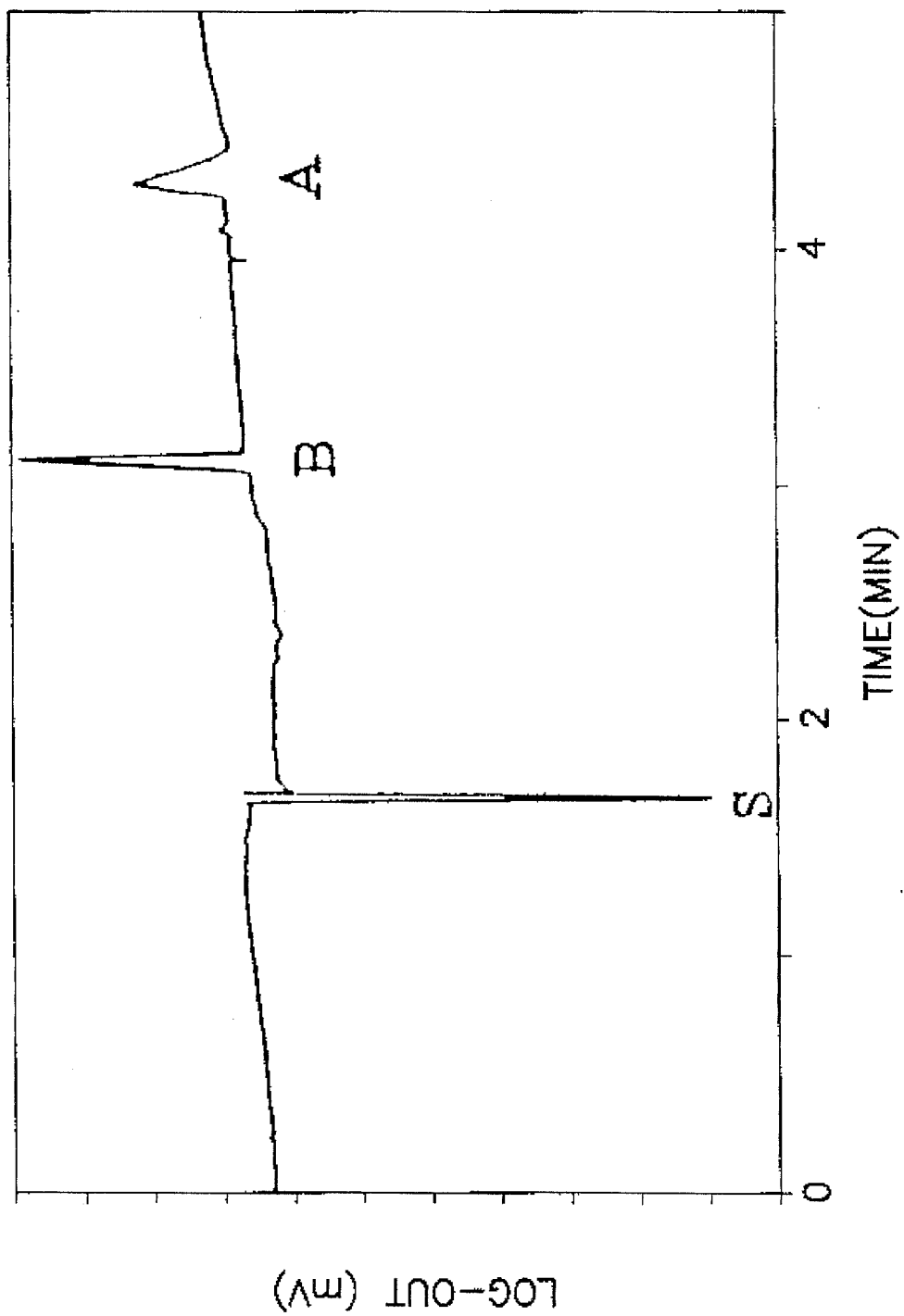
FIG. 11 is a graph of the log-out voltage versus time data of indirect absorption detection by analysis of $1.5 \times 10^{-5}$M pyruvic acid sodium salt and $1.5 \times 10^{-5}$M NPAS in CE using a NSCSS of the present invention.

FIG. 11 shows a graph of log-out voltage versus time data for a run with a 75 μm i.d. capillary using a NSCSS of the present invention. The sample injected into the capillary was a mixture of $1.5\times10^{-5}$M pyruvic acid sodium and $1.5\times10^{-5}$M NPAS. Peak (A) represents the pyruvate peak, (B), the NPAS peak, and (S), the system peaks. The NPAS eluted first and had a fairly sharp peak with a theoretical plates number of about $2\times10^4$. Pyruvic acid sodium salt eluted later, with a small amount of tailing, having a theoretical plates number of about $1\times10^4$.

For the 14 μm i.d. column, good separation was achieved for a sample composing $1.2\times10^{-4}$M pyruvic acid sodium salt and $5.2\times10^{-5}$M NPAS. This indicates the NSCSS is about 100 times more sensitive than presently available commercial systems.

EXAMPLE 7

Detection of Cation by Indirect Absorption Detection

Runs were conducted in a manner analogous to that of Example 4. A 40 cm total length, 33 cm effective length capillary of 75 μm i.d. was used. The separation buffer for cations was 0.5 nM malachite green (Lamda Physik, Acton, Mass.). The pH was 3 without further adjustments. Potassium nitrate was obtained from Aldrich. The potassium nitrate concentration in the sample injected was $4\times10^{-6}$M.

Figure 12:
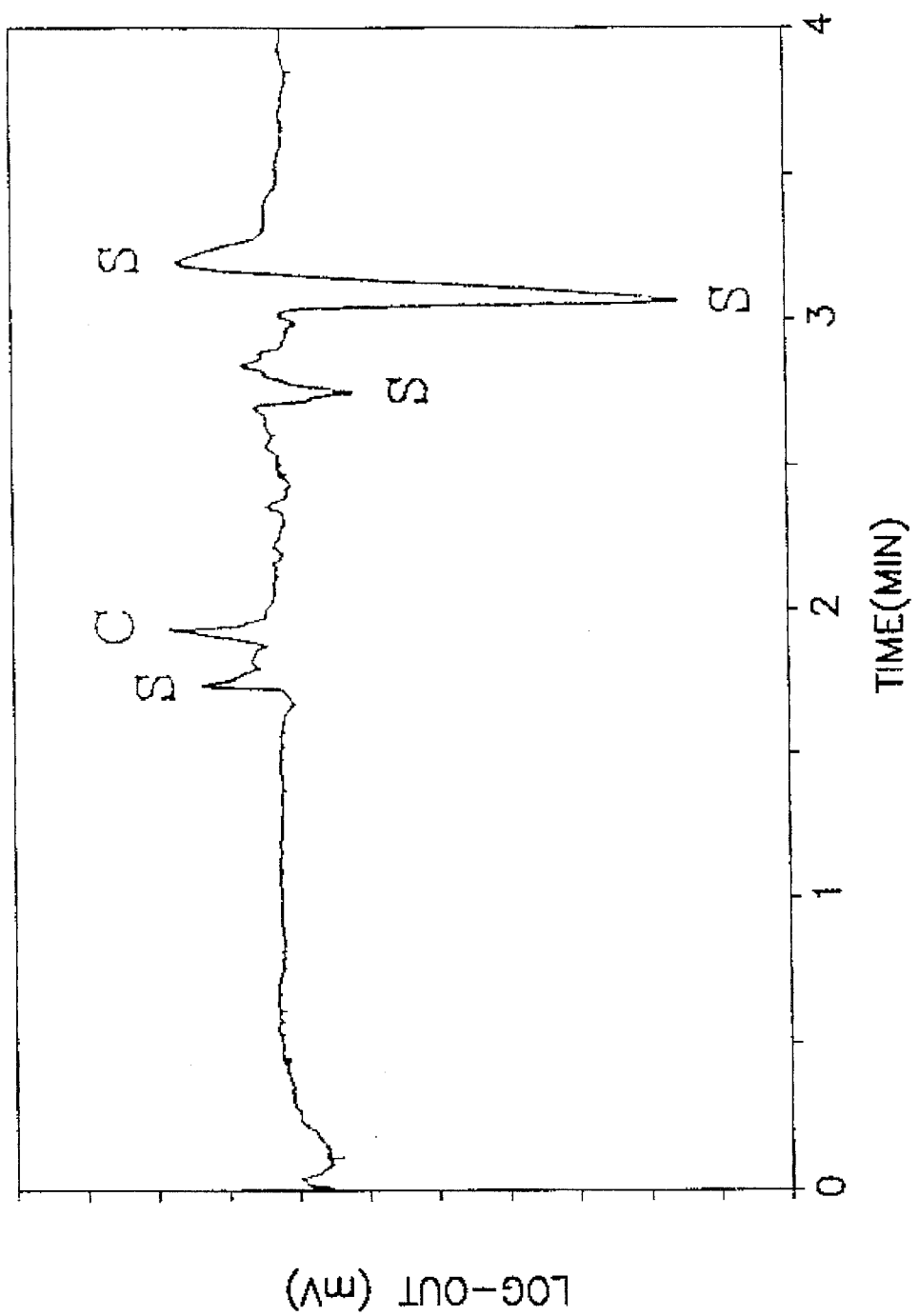
FIG. 12 is a graph of the log-out voltage versus time data of cation indirect absorption detection in the analysis of $4 \times 10^{-6}$M potassium nitrate in CE using a NSCSS of the present invention.

FIG. 12 is a graph of the log-out voltage versus time data. C is the $K^+$ peak, showing that the estimated detection limit for $K^+$ is about $1\times10^{-6}$M.

The present invention has been specifically described in the foregoing specification and embodiments. Although the preferred embodiments described are related to CE, analysis using LC can be analogously performed by a person skilled in the art. It is to be understood that the embodiments and methods described above are presented for illustrative purposes only and not be interpreted as limitations of the scope of the invention. It is possible to modify the details of the embodiments without departing from the spirit and scope of the present invention.

We claim:

1. A system for real-time detection of an analyte in a sample comprising:

(a) capillary separation means for moving the analyte through a capillary;

(b) light means for providing a coherent reference beam and a coherent sample beam, the sample beam irradiating the sample in the capillary and being of a wavelength at least partially absorbed by the sample;

(c) detector means for detecting the sample beam after it has travelled through the capillary and for detecting the reference beam, the detector means having a noise suppressing electrical circuit capable of noise suppression without signal averaging by electronically subtracting a reference current derived from the detected reference beam from a sample current derived from the sample beam, wherein the noise suppressing electrical circuit comprises:

(1) means for generating the sample current from the detected sample beam, the sample current representing an informational signal impressed on a steady state signal including a noise signal, the steady state signal corresponding to a steady state current;

(2) means for generating a reference current from the detected reference beam, the reference current representing a steady state current not including the informational signal;

(3) current dividing means for receiving and subdividing the larger of the sample current or reference current into a divided current having first and second components at a ratio determined by a control signal; and (4) combining means for combining the first component of the divided current with the undivided current to produce an output current in which the steady state current is substantially reduced and which further represents the informational signal of the sample current.

2. A system according to claim 1, wherein the noise suppressing electrical circuit further comprises feedback means for receiving an output signal from the combining means and controlling the signal dividing means to produce the first component of the divided current, such that when the first component of the divided current is combined with the undivided current, the steady state current of the output current is approximately zero.

3. A system according to claim 1, wherein the detector means further comprises a pair of unmatched photodiodes, one of the photodiodes detecting the sample beam and the other photodiode detecting the reference beam.

4. A system according to claim 1, further comprising collimating means for focusing the sample beam to a diameter of about 0.02 to about 0.25 of the inside diameter of the capillary.

5. A system according to claim 1, wherein the capillary has an inside diameter of about 20 μm or less.

6. A method for detecting an analyte in a sample, the method comprising:

(a) moving the analyte through a capillary of a capillary separation system;

(b) providing a coherent reference beam and a coherent sample beam, the sample beam irradiating the sample in the capillary, and being of a wavelength effective to be at least partially absorbed by the sample; and (c) detecting the reference beam and detecting the sample beam after transmission through the capillary;

(d) generating a sample current from the detected sample beam, the sample current representing an informational signal impressed on a steady state signal including a noise signal, the steady state signal corresponding to a steady state current;

(e) generating a reference current from the detected reference beam, the reference current representing a steady state current not including the informational signal;

(f) dividing the larger of the reference current or sample current to produce a divided current having first and second components; and (g) combining the first component of the divided current with the undivided current to produce an output current in which the steady state current is substantially reduced and which further represents the informational signal of the sample current.

7. A method according to claim 6, further comprising the step of providing a control signal to determine the ratio between the first and second components of the divided current, the control signal being chosen such that when the first component of the divided current is combined with the undivided current, the steady state current of the output current is approximately zero.

8. A method according to claim 6, wherein the steps of detecting the reference and sample beams further comprises detecting the reference and sample beams with a pair of unmatched photodiodes, one of the photodiodes detecting the sample beam and the other photodiode detecting the reference beam.

9. A method according to claim 8, wherein each of the pair of photodiodes is operated in its linear range.

10. A method according to claim 6, wherein the step of providing a coherent reference beam and a coherent signal beam further comprises collimating the sample beam to a diameter of about 0.02 to about 0.25 of the inside diameter of the capillary.

11. A method according to claim 6, wherein the step of moving analyte through the capillary further comprises:

a) providing a capillary with a selected portion through which the transmitted light can be detected;

b) providing a sample of a solution to be tested for the analyte;

c) providing a buffer solution with a selected concentration of a chromophore; and d) applying a high voltage through the capillary to move the chromophore of the buffer solution through the capillary; wherein there is a displacement or ion-pairing of the analyte and the chromophore in the buffer solution in the capillary.

12. A method according to claim 6, wherein the step of moving analyte through the capillary comprises:

a) providing a capillary with a selected portion through which the transmitted light can be detected;

b) providing a sample of a solution to be tested for the analyte, the analyte being labelled with a chromophore;

c) providing a buffer solution;

d) applying a high voltage through the capillary to move ions in the buffer solution through the capillary; and e) supplying the sample to the capillary filled with the buffer solution.

13. A method according to claim 6, wherein the step of moving an analyte through a capillary comprises moving the analyte through a liquid chromatographic apparatus.

14. A method according to claim 6, wherein the step of moving an analyte through a capillary comprises moving the analyte through a silated capillary.

15. A method according to claim 6, wherein the step of providing the reference and signal beams further comprises splitting a single coherent light beam into the reference and signal beams.

16. A method according to claim 6, wherein the analyte is a biochemical substance.

17. A method according to claim 6, wherein the analyte is derived from a member selected from the group consisting of polypeptides, polynucleotides, carbohydrates, cells, bacteria and viruses.

18. A method for detecting an analyte in a sample, the method comprising:

(a) moving the analyte through a capillary of a capillary separation system;

(b) providing coherent light beam and splitting the coherent light beam into a reference beam and a sample beam, the sample beam irradiating the sample in the capillary, and being of a wavelength effective to be at least partially absorbed by the sample; and (c) detecting the reference beam using a reference photodiode and detecting the sample beam after transmission through the capillary using a sample photodiode, the reference and sample photodiodes operating in their respective linear ranges;

(d) generating a sample current from the detected sample beam, the sample current representing an informational signal impressed on a steady state signal including a noise signal, the steady state signal corresponding to a steady state current:

(e) generating a reference current from the detected reference beam, the reference current representing a steady state current not including the informational signal;

(f) dividing the larger of the reference current or sample current to produce a divided current having first and second components;

(g) providing a control signal to determine the ratio between the first and second components of the divided current, the control signal being chosen such that a steady state current of the first component is substantially equal to a steady state current of the undivided current; and (h) combining the first component of the divided current with the undivided current to produce an output current in which the steady state current is approximately zero and which further substantially represents the informational signal of the sample current.

* * * * *